(12) United States Patent
McDevitt

(10) Patent No.: US 8,680,145 B1
(45) Date of Patent: Mar. 25, 2014

(54) COMPOSITIONS AND METHODS FOR TREATMENT OF FEAR OF MEDICAL PROCEDURES

(71) Applicant: Jason P. McDevitt, Williamsburg, VA (US)

(72) Inventor: Jason P. McDevitt, Williamsburg, VA (US)

(73) Assignee: College of William and Mary, Williamsburg, VA (US)

( * ) Notice: Subject to any disclaimer, the term of this patent is extended or adjusted under 35 U.S.C. 154(b) by 0 days.

(21) Appl. No.: 13/857,532

(22) Filed: Apr. 5, 2013

(51) Int. Cl.
*A61K 31/197* (2006.01)

(52) U.S. Cl.
USPC .......................................................... 514/563

(58) Field of Classification Search
None
See application file for complete search history.

(56) References Cited

U.S. PATENT DOCUMENTS

| | | | |
|---|---|---|---|
| 4,576,951 A | | 3/1986 | Rovati |
| 5,084,007 A | * | 1/1992 | Malin et al. ...................... 604/20 |

OTHER PUBLICATIONS

Benedetti et al., "The Biochemical and Neuroendocrine Bases of the Hyperalgesic Nocebo Effect", The Journal of Neuroscience (2006), vol. 26(46), p. 12014-12022.
Benedetti et al., "Potentiation of Placebo Analgesia by Proglumide", Lancet (1995), vol. 346, p. 1231.
Benedetti et al., "Blockade of nocebo hyperalgesia by the cholecystokininantagonist proglumide", Pain (1997), vol. 71, p. 135-140.
Bernstein et al., "Proglumide as a Morphine Adjunct in Cancer Pain Management", Journal of Pain and Symptom Management (1998), vol. 15(5), p. 314-320.
Cohen et al., "CCK-Antagonists in a Rat Exposed to Acute Stress: Implication for Anxiety Associated with Post-Traumatic Stress Disorder", Depression and Anxiety (1999), vol. 10, p. 8-17.
Itoh et al., "Effect of Cholecystokinin OctapeptideAntagonists on the Extinction of an Active Avoidance Task in the Rat", Drug Development Research (1989) vol. 17, p. 83-87.
Lehmann et al., "Failure of Proglumide, a Cholecystokinin Antagonist, to Potentiate Clinical Morphine Analgesia", Anesth. Analg. (1989), vol. 68, p. 51-56.
McCleane, "The Cholecystokinin Antagonist Proglumide Enhances the Analgesic Efficacy of Morphine in Humans with Chronic Benign Pain", Anesth. Analg. (1998), vol. 87, p. 1117-1120.
Watkins et al., "Multiple Endogenous Opiate and Non-Opiate Analgesia Systems: Evidence of Their Existence and Clinical Implications", Annals New York Academy of Sciences (1986), vol. 467, p. 273-299.
Woodruff et al., "Cholecystokinin Antagonists", Annu. Rev. Pharmacol. Toxicol. (1991), vol. 31, p. 469-501.
Choy et al., "Treatment of Specific Phobia in Adults", Clinical Psychology Review (2007), vol. 27, p. 1266-1286.
Myers et al., "Glutamate Receptors in Extinction and Extinction-Based Therapies for Psychiatric Illness", Neuropsychopharmacology Reviews (2010), p. 1-20.

* cited by examiner

*Primary Examiner* — Jeffrey E Russel
(74) *Attorney, Agent, or Firm* — Jason P. McDevitt

(57) ABSTRACT

The invention describes methods and compositions for treating fear of medical procedures comprising administering proglumide to a patient having fear of medical procedures, followed by subjecting the patient to the fear-inducing medical procedure. Representative examples of fear of medical procedures that can be treated according to the methods and compositions described herein include: dental phobia, fear of needles, fear of surgery, and fear of childbirth.

14 Claims, No Drawings

COMPOSITIONS AND METHODS FOR TREATMENT OF FEAR OF MEDICAL PROCEDURES

CROSS-REFERENCE TO RELATED APPLICATIONS

Not applicable

STATEMENT REGARDING FEDERALLY SPONSORED RESEARCH OR DEVELOPMENT

Not applicable

BACKGROUND OF THE INVENTION

Proglumide is a drug that has been approved for use in many countries as a treatment for stomach ulcers. It is not approved for use in the United States, and is no longer frequently prescribed internationally, with newer anti-ulcer drugs preferred. Proglumide inhibits gastrointestinal mobility and acts as a cholecystokinin antagonist, blocking both the $CCK_A$ and $CCK_B$ subtypes.

Cholecystokinin (CCK) is widely distributed in the central nervous system, and its levels increase with chronic opiate administration. Increased levels of CCK are believed to reduce the analgesic effect of opiates, and also are believed to be at least partially responsible for tolerance to opiate analgesics such as morphine.

Since proglumide is a CCK antagonist (albeit a moderate, non-selective one), it has been widely studied for its potential role in enhancing opiate efficacy and/or reducing opiate tolerance. For example, studies have determined that proglumide enhances the analgesic efficacy of morphine in treating human patients with chronic pain (McCleane, G., "The cholecystokinin antagonist proglumide enhances the analgesic efficacy of morphine in humans with chronic benign pain", *Anesth. Analg.* (1998) 87:1117-20), and also potentiates morphine analgesia in both opiate-naïve and morphine-tolerant rats (Watkins, L. R. et al., "The enhancement of opiate analgesia and the possible reversal of morphine tolerance by proglumide", *Annals of the New York Academy of Sciences* (1985), 448 (Neuronal Cholecystokinin), 676-7). Other studies have observed no difference between treatment and control groups in studies examining whether proglumide augments morphine analgesia in cancer pain management (Bernstein, Z. P. et al., "Proglumide as a morphine adjunct in cancer pain management", *Journal of Pain and Symptom Management* (1998), 15(5), 314-20) and in post-operative patients (Lehmann, K. A. et al., "Failure of proglumide, a cholecystokinin antagonist, to potentiate clinical morphine analgesia. A randomized doubleblind postoperative study using patient-controlled analgesia (PCA)", *Anesthesia and Analgesia* (1989), 68(1), 51-6).

The placebo effect is a psychobiological phenomenon that is attributable to different mechanisms, including expectation of clinical improvement and Pavlovian conditioning. Endogenous opioids have a significant role in placebo analgesia, although non-opioid mechanisms can also play a significant role (Benedetti, F. et al., "Neurobiological Mechanisms of the Placebo Effect", *Journal of Neuroscience* (2005), 25(45): 10390-10402). The effect of endogenous opioids is balanced by the anti-opioid action of CCK. The CCK antagonist proglumide was shown to enhance placebo analgesia (Benedetti, F. et al., "Potentiation of placebo analgesia by proglumide" (1995), *Lancet* 346: 1231) and block nocebo hyperalgesia (Benedetti, F. et al., "The biochemical and neuroendocrine bases of the hyperalgesic nocebo effect" (2006), *Journal of Neuroscience*, 26(46):12014-12022).

A significant downside of proglumide is the rapidity with which humans become habituated. While proglumide has been suggested for use in reducing tolerance to opioids, rapid buildup of tolerance to proglumide can be quite problematic. Proglumide has been demonstrated to be ineffective as a long-term adjunct to opiate treatment for chronic pain (Kellstein, D. E., et al., "Chronic administration of cholecystokinin antagonists reverses the enhancement of spinal morphine analgesia induced by acute pretreatment" (1990), *Brain Research*, 516(2): 263-270). This is unfortunate, as in many cases, a patient's anxiety about chronic pain significantly contributes to the pain experienced by the patient.

While proglumide is a drug that has a good safety record and has a number of interesting properties as described above, it is not approved by FDA. To our knowledge, while proglumide has been suggested as a treatment for other anxiety disorders, it has not been used specifically as a treatment for specific phobia, or administered on a non-chronic basis for the treatment of specific phobias, and moreover, it has not been used as a treatment for fear of medical procedures.

BRIEF SUMMARY OF THE INVENTION

The invention describes methods for treatment of fear of medical procedures comprising administering proglumide, or a pharmaceutically acceptable salt thereof, to a human subject having fear of a medical procedure, wherein said human subject commences said fear-inducing medical procedure within 12 hours before or after being administered proglumide. If administered to individuals not having fear of a medical procedure, proglumide would have little or no effect on the observed pain resulting from the medical procedure. It is not an analgesic in and of itself. However, proglumide reduces the increase in pain that can be attributed to the anxiety about the pain, and hence it has the benefit to the patient of reducing pain from a medical procedure, increasing medical compliance, serving as form of exposure therapy to alleviate the anxiety associated with the medical procedure, and providing additional benefits associated with antagonizing CCK effects depending on the specific medical procedure.

In a representative embodiment, patients having dental phobia are administered proglumide within 12 hours prior to a dental appointment.

In a representative embodiment, a pregnant woman having significant fear of labor and delivery, for example a woman with tokophobia, is administered proglumide once labor commences, and prior to the birth of the child. In addition to reducing the pain associated with labor and childbirth, administration of proglumide can have numerous other indirect benefits; for example, by reducing pain, it can make it less likely that a pregnant woman chooses to have other pain medications, such as epidural anesthesia, thereby avoiding some of the downsides of epidurals such as longer labors, longer pushing, increased risk of vacuum, forceps, and Caesarean sections, as well as increased risk of other complications, such as low blood pressure (which might adversely affect the baby), fever, headache, and nerve damage.

In a representative embodiment, a patient having tomophobia (a fear of invasive medical procedures such as surgery) is administered proglumide within 12 hours prior to the commencement of a scheduled surgery (e.g., knee replacement surgery).

In a representative embodiment, a patient having trypanophobia (fear of needles) and having an additional medical condition that requires weekly or monthly shots self-administers proglumide within 12 hours prior to administering the injection. In another representative embodiment, a patient having trypanophobia (fear of needles) and having an additional medical condition (e.g., cancer) that requires intravenous (IV) infusions self-administers proglumide within 12 hours prior to introduction of an IV catheter.

According to the methods of the invention, proglumide is administered, preferably by oral or sublingual route, at a dose of between 0.5 mg and 500 mg. Multiple doses may be administered within 12 hours of the commencement of the fear-inducing medical procedure. However, it is important that proglumide not be administered on a chronic basis, as tolerance rapidly develops. Accordingly, the methods of the invention contemplate administering proglumide within 12 hours of the commencement of the fear-inducing medical procedure, but disclaim administration of proglumide on an extended daily basis before such time, or after such time. For example, administering proglumide to a patient with dental phobia on a daily basis for a week, wherein on the 7$^{th}$ day the patient has a dental appointment, would not be covered by the methods of the invention, and would not provide the significant benefits attributable to the methods of the invention, as the subject can habituate to proglumide in that time, and thus the effect of the proglumide would be diminished. More specifically, the methods of the invention contemplate administering proglumide prior to commencement of the fear-inducing medical procedure, wherein said administering of proglumide is not part of a sequence of daily administration of proglumide lasting more than four consecutive days.

Fear of medical procedures is often classified as a specific phobia, and psychological treatments are the current treatment of choice for specific phobia, including for example, exposure-based psychotherapy (e.g., cognitive behavioral therapy). The premise of exposure-based psychotherapy for specific phobias is that a patient is exposed to a fearful stimulus, and learns a new, less fearful response to the stimulus, thereby reducing the patient's fear of, and tendency to avoid, the stimulus. By administering proglumide to patients having a fear of medical procedures, prior to commencing the fear-inducing medical procedure, the component of pain attributable to anxiety is reduced, and thus the patient experiences less pain. Endogenous opioids (e.g., endorphins) released during high-stress situations serve to reduce the pain, and are normally counteracted by CCK. By inhibiting CCK, proglumide enhances the pain-reducing properties of the endorphins, and also enhances the general feeling of well-being provided by endorphins. This feeling of well-being is one that humans often seek to replicate (e.g., the so-called "runner's high"), and thus administering proglumide to a human subject to treat fear of medical procedures, followed by the subject's undergoing the fear-inducing medical procedure, serves as a form of exposure therapy wherein the abnormal, high-pain response previously associated with the stimulus is replaced by a lowered-pain, exaggerated endorphin response that is not as bad as expected and can therefore reduce the subject's fear of the medical procedure in the future.

Pharmaceutical compositions for the treatment of fear of medical procedures comprising proglumide, or a pharmaceutically acceptable salt thereof, are described herein.

BRIEF DESCRIPTION OF THE DRAWING

Not applicable.

DETAILED DESCRIPTION OF THE INVENTION

As used herein, each of the following terms has the meaning associated with it as described below.

The articles "a" and "an" are used herein to refer to one or to more than one (i.e. to at least one) of the grammatical object of the article. By way of example, "an element" means one element or more than one element.

As used herein, "plurality" means at least two.

As used herein, "FDA" means the United States Food and Drug Administration.

Any ranges cited herein are inclusive, e.g., "between about 50 mg and 100 mg" includes compositions of 50 mg and 100 mg.

As used herein, a subject is "treated", or subjected to "treatment", when an earnest attempt is made to alleviate a medical disorder or disease. For example, a subject can be treated for a disorder by being administered a pharmacologic agent that is intended to alleviate the disorder, irrespective of whether the treatment actually was successful in alleviating the disorder.

As used herein, a disease or disorder or medical affliction is "alleviated" if either the severity of a symptom of the disease or disorder or medical affliction, the frequency with which such a symptom is experienced by a subject, or both, are reduced.

A "subject" of diagnosis or treatment is a human.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

As used herein, "fear of medical procedures", also referred to as "medical fear", means fear of any experience that involves medical personnel or procedures involved in the process of evaluating or modifying health status in traditional health care settings (Marion E. Broome and Teri Mobley (2003). "The Child Medical Fear Scale". In Carolyn F. Waltz, Colleen Dilorio, and Ora L. Strickland. *Measurement of Nursing Outcomes*. Springer Publishing Company, p. 197).

Fear of medical procedures is often classified as a specific phobia (specifically, a blood-injection-injury subtype of specific phobias). Specific phobia is a type of anxiety disorder. Some common specific phobias include fear of heights (acrophobia), fear of small confined spaces (claustrophobia), and fear of spiders (arachnophobia). Psychological treatments such as exposure-based psychotherapy (e.g., cognitive behavioral therapy) are the current treatment of choice for specific phobias. Representative examples of fear of medical procedures that can be treated according to the methods and compositions described herein include, but are not limited to: dental fear or dental phobia, fear of doctors, trypanophobia or fear of needles, tomophobia or fear of surgery, and tokophobia or fear of childbirth.

The methods and compositions described herein may generally be useful for treating specific phobias, and can have modest benefits across a range of specific phobias. For example, a patient with arachnophobia could take proglumide, and then undergo formal or informal exposure therapy involving spiders. Relative to equivalent exposure therapy in the absence of proglumide, the patient could realize increased benefits based on a proglumide-mediated enhanced response to endogeneous opioids, thereby increasing the effectiveness of the exposure therapy. That said, among the broad range of specific phobias, the methods and compositions described herein are most useful, and provide significantly greater benefits, for treatment of specific phobias falling within the blood-injection-injury subtype, and specifically within fear of medical procedures. An individual may have a single disorder, or may have a constellation of disorders that can be treated by the methods described herein.

In representative embodiments, medical afflictions that can be treated by the methods and compositions disclosed herein are recurring or chronic disorders in a human in which anxiety about pain that a subject associates with a medical affliction amplifies the pain experienced by a subject. For example, one such embodiment is agliophobia, or fear of pain. In preferred embodiments, the methods and compositions disclosed herein are used to treat fear of medical procedures. Note that while fear of medical procedures can be classified as a specific phobia, such classification is not necessary. Specific phobias are often defined as an unreasonable or irrational fear related to exposure to specific objects or situations. However, given the potential complications and the well-known pain associated with childbirth, for example, a substantial and deleterious fear of childbirth might actually be considered reasonable and rational, depending on the situation. Irrespective of whether a particular fear of medical procedures is deemed rational or irrational, and irrespective if it is formally diagnosed as a specific phobia, a fear of medical procedures can still be deleterious to the subject and can match the symptoms and disadvantages of a specific phobia. Fortunately, in such cases, the fear of medical procedures can be treated efficaciously with the methods and compositions described herein.

Many individuals suffer from pain, including chronic pain which can have many different causes. Pain ordinarily serves a protective role, and goes away after the healing process is complete. However, sometimes pain persists long after its protective function is no longer necessary, morphing into chronic pain and causing pathological changes to the central nervous system. As used herein, pain means "an unpleasant sensory and emotional experience associated with actual or potential tissue damage or described in terms of such damage", which is the definition that has been given by the International Association for the Study of Pain.

Studies (*Science*, Vol 303, 1162-1167 (2004)) have demonstrated that people experience pain differently when they believe that the pain will be alleviated. The experience of pain arises from both physiological and psychological factors, including one's beliefs and expectations. Given this result, it is clear that a subject's response to painful stimuli is governed by a number of factors, many of which are psychological. If a subject is anxious about the pain, the pain that is experienced is normally worse than if the subject is not anxious about the pain. Not surprisingly, pain has been treated effectively using cognitive behavioral therapy. Administration of a drug that reduces pain can alter a subject's response to pain in a beneficial manner.

In one embodiment, a pregnant woman having fear of medical procedures, specifically fear of labor and delivery, for example a woman with tokophobia, is administered proglumide after labor commences and prior to the birth of the child. In addition to reducing the pain associated with labor and childbirth, administration of proglumide can have numerous other indirect benefits; for example, by reducing pain, it can make it less likely that a pregnant woman chooses to have other pain medications, such as epidural anesthesia. In a retrospective study of 202 parturient labors conducted by McRae-Bergeron et al. of the Uniformed Services University of the Health Science in Bethesda, Md., comparing outcomes from women who received epidural amnesia and women who chose either unmedicated childbirth, IV narcotics, or pudendal block, the epidural group experienced a significantly longer second stage labor, and were 3.5 times more likely to have oxytocin induction and 4.5 times more likely to have instrument-assisted delivery (McRae-Bergeron, C E, et al., "The effect of epidural analgesia on the second stage of labor", *AANA J.* 1998 April; 66(2):177-82.).

In a planned clinical study, pregnant subjects will receive placebo or proglumide (100 mg) after hospital admission and commencement of labor. Subjects will subsequently choose whether to have additional pain medication, and the following outcomes will be assessed: duration of labor, likelihood of oxytocin administration, likelihood of administering additional pain medication, likelihood of administering epidural analgesia, likelihood of instrument-assisted delivery, likelihood of Caesarean section, and risk of complications such as low blood pressure and nerve damage. It is expected that, relative to subjects administered placebo, subjects administered proglumide will have one or more of: shorter labors, reduced likelihood of being administered oxytocin, reduced need for additional pain medication, reduced likelihood of epidural analgesia, and reduced likelihood of experiencing complications associated with these options. Furthermore, relative to subjects administered plabebo, subjects administered proglumide may be: more likely to view the birth experience in a more positive manner, less fearful of subsequent childbirths, and less likely to experience post-partum depression. Accordingly, administration of proglumide prior to childbirth can increase a mother's positive feelings, reduce medical complications, and/or reduce costs associated with childbirth.

In another embodiment, an individual with fear of medical procedures, specifically dental fear, is administered proglumide the morning of a scheduled dental appointment.

In a proposed clinical trial, subjects having dental fear are administered placebo or proglumide (200 mg) two hours prior to the start of standard dental checkups (e.g., cleaning and examination). Subsequent to the dental checkup, subjects are asked to rate the level of pain they experienced during the dental checkup, as well as their anxiety about future dental visits. Relative to subjects administered plabebo, subjects administered proglumide are expected to experience reduced pain levels during the dental checkup, and are expected to have reduced anxiety about and during a subsequent dental visit.

In another embodiment, an individual with fear of medical procedures, specifically a fear of needles, and who requires periodic parenteral delivery of pharmaceuticals, self-administers proglumide (50 mg) prior to self-injection of the pharmaceutical. For example, many individuals with diseases such as multiple sclerosis, lupus, diabetes, cancer, rheumatoid arthritis, and chronic idiopathic thrombocytopenic purpura require periodic (e.g., weekly, monthly, etc.) parenteral administration of drugs to treat those conditions, or alternatively, avoid periodic parenteral administrations of drugs and instead choose alternative drugs or therapies that may be less effective. For individuals with fear of needles, the periodic parenteral injections are a particularly difficult process, and reducing the pain and/or anxiety associated with the parenteral injections can increase patient compliance such that subsequent doses are less likely to be skipped or delayed. Many other individuals with fear of needles must undergo periodic medical procedures that require intraveneous catheterization, and such individuals can benefit from administration of proglumide prior to insertion of the IV catheter.

In another embodiment, a patient with fear of medical procedures, specifically tomophobia (fear of surgery), is administered proglumide several hours prior to the start of a scheduled surgery. As a result, post-surgical pain can be reduced, potentially leading to reduced use of opiate narcotics during recovery, and reduced likelihood of complications stemming from addiction to painkillers. In some cases, it may be advantageous to administer proglumide for a short time after surgery as well.

Formulation of Pharmaceutical Compositions

Pharmaceutical compositions contemplated by the methods and compositions of the invention may be formulated and administered to a subject for treatment of the diseases or afflictions disclosed herein as described below.

The invention encompasses the preparation and use of proglumide pharmaceutical compositions as an active ingredient useful for treatment of the diseases and disorders disclosed herein. Such a pharmaceutical composition may consist of the active ingredient(s) alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

The compounds of the invention are also useful when formulated as salts. In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable acid addition salts of inorganic acids may also be formed, including hydrochloride, sulfate, nitrate, bicarbonate, and carbonate salts. Pharmaceutically acceptable salts may be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

The descriptions of pharmaceutical compositions provided herein are directed to pharmaceutical compositions which are suitable for ethical administration to humans.

Pharmaceutical compositions that are useful in the methods of the invention may be prepared, packaged, or sold in formulations suitable for oral, rectal, vaginal, parenteral, sublingual, topical, pulmonary, intranasal, buccal, ophthalmic, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

The therapeutically effective dose of the pharmacologic agent can be administered using any medically acceptable mode of administration. Although the skilled artisan would contemplate any of the modes of administration known to one of ordinary skill, preferably the pharmacologic agent is administered according to the recommended mode of administration, for example, the mode of administration listed on the package insert of a commercially available agent.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of a dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or gel or cream or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken, i.e., by rapid inhalation through the nasal passage from a container of the powder.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein.

Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1-1.0% (w/w) solution or suspension of the active ingredient in an aqueous or oily liquid carrier. Such drops may further comprise buffering agents, salts, or one or more other of the additional ingredients described herein. Other opthalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, *Remington's Pharmaceutical Sciences*, Mack Publishing Co., Easton, Pa., which is incorporated herein by reference.

Dosage

For treatment of fear of medical procedures, proglumide dosage levels can be between about 0.5 mg and 500 mg when administered to adult subjects. The therapeutically effective dose of the pharmacologic agent can be administered using any medically acceptable mode of administration. Although the skilled artisan would contemplate any of the modes of administration known to one of ordinary skill, preferably the pharmacologic agent is administered according to the recommended mode of administration, for example, the mode of administration listed on the package insert of a commercially available agent.

In one embodiment, proglumide tablets useful for treating fear of medical procedures can be made by: (1) mixing 2500 g proglumide, 600 g lactose, and 700 g starch, then adding 300 g of wet starch and mixing to homogeneity; (2) grounding the resultant mass while wet, passing through a 15 mesh sieve, and mixing with 50 g talc, 20 g magnesium stearate, and 30 g silicon dioxide; and (3) compressing the mixture in a rotary compressor and tableting to provide 10,000 tablets each weighing 420 mg and comprising 250 mg proglumide, 60 mg lactose, 100 mg starch, 5 mg talc, 2 mg magnesium stearate, and 3 mg silicon dioxide. Smaller tablets can be made from the same mixture, each comprising from 5 to 200 mg proglumide.

In another embodiment, a mixture of 75 g of proglumide, 75 g of lactose and 100 g of talc can be combined, mixed, wetted with a sufficient quantity of alcohol and granulated followed by drying. The obtained granulate can be filled into capsules containing, for example, 10 mg, 25 mg, 50 mg, 75 mg, 100 mg, or 200 mg proglumide. The pharmaceutical compositions can be useful for treating fear of medical procedures.

In another embodiment, a composition for IV injection can be made as follows: add 4263 g of the sodium salt of proglumide to 15 L of water and 93 g of ethanolamine and stir until a clear solution is obtained. After buffering with citric acid, the solution is diluted to a volume of 30 L, then filtered under pressure in an inert gas into 40,000 glass vials which are sterilized under heat, yielding 40,000 vials each containing 106.6 mg sodium proglumide, equivalent to 100 mg proglumide.

Timing and Frequency of Dosage

According to the methods described herein for treating fear of medical procedures, proglumide is initially administered to a patient within about 12 hours prior to commencement of the medical procedure of which the patient has fear, and can be administered again subsequent to said initial administration. In preferred embodiments, the administered proglumide is absorbed and at therapeutically effective levels in the brain when the fear-inducing medical procedure is commenced. However, for certain medical procedures that can take a particularly long time, initial administration of proglumide can occur after commencement of the medical procedure, but prior to termination of the medical procedure. For example, proglumide can be administered after the start of labor, but prior to childbirth. Moreover, proglumide could be administered multiple times during a long labor according to the methods of the invention.

Importantly, proglumide rapidly induces tolerance, and administration of proglumide on an extended daily basis (i.e., for more than four consecutive days) would not provide the benefits obtained by administering proglumide within 12 hours prior to commencement of a fear-inducing medical procedure. Furthermore, administering proglumide for four consecutive days, followed by a day off, followed by administering proglumide for an additional four consecutive days, one of which administrations was within 12 hours prior to commencement of a fear-inducing medical procedure, would also not provide the benefits recited herein. The benefits recited herein, obtained by administering proglumide to a subject within 12 hours prior to commencement of a medical procedure of which the subject has fear, are not obtained if the subject has a significant tolerance for proglumide, which is increasingly likely to occur if proglumide has been administered more than four days in a row, or more than 7 days within the last 30 days. In preferred embodiments, when the subject having a fear of medical procedures is administered proglumide within 12 hours prior to commencement of the fear-inducing medical procedure, the subject has not previously been administered proglumide on more than one other day in the previous seven days, and is not administered proglumide on more than one other day in the seven days following said fear-inducing medical procedure.

EXAMPLES

The invention is now described with reference to the following examples. These examples are provided for the purpose of illustration only and the invention should in no way be construed as being limited to these examples but rather should be construed to encompass any and all variations which become evident as a result of the teaching provided herein.

Proglumide was obtained from commercial suppliers and/or pharmacies, and loaded into capsules.

Example 1

A subject with dental phobia, who had not been to a dentist in many years, agreed to undergo a routine dental checkup visit (cleaning and examination), and to take proglumide prior to the dental visit. A capsule containing 100 mg proglumide and inactive ingredients was administered to the subject ninety minutes prior to the dental appointment. Subject-reported pain during the never-pleasant calculus removal process was substantially reduced relative to previous dental visits in which proglumide had not been taken beforehand, in spite of the extended duration of the cleaning process since there were many years worth of calculus to remove. Total discomfort was low enough that the subject would be willing to return to a regular dental checkup schedule provided proglumide was taken beforehand each dental checkup, at least at the outset. Furthermore, the subject was willing to return for a follow-up visit within one week in order to replace an aged filling, a procedure that was not deemed urgent and easily could have been delayed. Additionally, the post-checkup pain experienced by the subject (e.g., tender gums, sensitivity while chewing) was significantly reduced relative to that experienced after previous dental checkups.

This is the first experimental demonstration that proglumide, taken prior to a fear-inducing medical procedure while not being administered on a long-term basis, can act in conjunction with the fear-inducing medical procedure as a successful form of exposure therapy.

Example 2

The same subject as in Example 1 returned to the dentist five days after the dental checkup of Example 1 in order to replace an aged metal filling. Again, proglumide was administered to the subject in advance of the appointment. A capsule containing 200 mg proglumide and inactive ingredients was administered to the subject 90 minutes prior to the dental appointment. The dentist administered a local anesthetic (e.g., lidocaine) painkiller as part of the procedure for replacing the filling. The residual discomfort following the procedure, including after the numbness wore off, was mild.

INCORPORATION BY REFERENCE

All publications, patents, and patent applications cited herein are hereby expressly incorporated by reference in their entirety and for all purposes to the same extent as if each was so individually denoted.

EQUIVALENTS

While specific embodiments of the subject invention have been discussed, the above specification is illustrative and not restrictive. Many variations of the invention will become apparent to those skilled in the art upon review of this specification. Contemplated equivalents of the methods of treating anxiety related disorders disclosed here include administering fast acting compositions which otherwise correspond thereto, and which have the same general properties thereof, wherein one or more simple variations of substituents or components are made which do not adversely affect the characteristics of the methods and compositions of interest. The full scope of the invention should be determined by reference to the claims, along with their full scope of equivalents, and the specification, along with such variations.

I claim:

1. A method for treating fear of medical procedures in a human subject which comprises the following steps:
(i) administering to the subject a therapeutically effective amount of proglumide, or pharmaceutically acceptable salt thereof, and
(ii) subjecting the subject to a medical procedure of which said subject has a fear;
wherein said proglumide is administered within 12 hours prior to commencement of said medical procedure of which said subject has a fear;
wherein said administering of said proglumide is not part of a sequence of daily administration of proglumide lasting more than four consecutive days
and wherein the fear of medical procedures is a specific phobia.

2. The method of claim 1, wherein the fear of medical procedures is a specific phobia selected from the group consisting of fear of childbirth, fear of needle injection, dental fear, and fear of surgery.

3. The method of claim 1, wherein said subject has tokophobia, and wherein said proglumide is administered to said subject after commencement of labor and prior to childbirth.

4. The method of claim 3, wherein said subject to whom proglumide is administered prior to childbirth experiences one or more benefits selected from the group consisting of: reduced pain during labor, reduced duration of labor, reduced likelihood of being administered supplemental pain medication, reduced likelihood of epidural anesthesia, reduced likelihood of instrument-assisted delivery, and reduced likelihood of Caesarean section delivery.

5. The method of claim 1, wherein said proglumide is administered at a dose between about 0.5 mg and 500 mg.

6. The method of claim 5, wherein said proglumide is administered at a dose between about 5 mg and 200 mg.

7. A method for treating specific phobia in a human subject using an exposure-based process which comprises the following steps:
(i) administering to the subject a therapeutically effective amount of proglumide, or pharmaceutically acceptable salt thereof, and
(ii) exposing the subject to a stimulus that induces a fear response related to the subject's specific phobia;
wherein said proglumide is administered within 12 hours prior to commencement of said step of exposing;
wherein said administering of said proglumide is not part of a sequence of daily administration of proglumide lasting more than four consecutive days; and
wherein said subject's subsequent fear responses to said stimulus have a reduced intensity.

8. The method of claim 7, wherein said specific phobia comprises a fear of needle injection.

9. The method of claim 7, wherein said specific phobia comprises dental fear.

10. The method of claim 7, wherein said specific phobia comprises tokophobia.

11. A method for facilitating labor and delivery associated with childbirth comprising administering to a pregnant female having a specific fear of medical procedures, after commencement of labor and prior to delivery, a therapeutically effective amount of proglumide, or pharmaceutically acceptable salt thereof;
wherein said administering of said proglumide is not part of a sequence of daily administration of proglumide lasting more than four consecutive days.

12. The method of claim 11, wherein said step of administering reduces the likelihood of a complication during labor or delivery; and
wherein said complication is selected from the group consisting of instrument-assisted delivery, administration of supplemental oxytocin, excessive duration of labor, and Caesarean section delivery.

13. The method of claim 12, wherein said complication during labor or delivery is administration of supplemental oxytocin.

14. The method of claim 12, wherein said complication during labor or delivery is instrument-assisted delivery.

* * * * *